(12) United States Patent
Dennerlein et al.

(10) Patent No.: US 8,630,474 B2
(45) Date of Patent: Jan. 14, 2014

(54) BACK-PROJECTION OF A PROJECTION IMAGE DATA SET WITH DEPTH-DEPENDENT FILTERING

(75) Inventors: Frank Dennerlein, Forchheim (DE); Frederic Noo, Midvale, UT (US)

(73) Assignees: Siemens Aktiengesellschaft, Munich (DE); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/537,298

(22) Filed: Jun. 29, 2012

(65) Prior Publication Data

US 2013/0028498 A1 Jan. 31, 2013

Related U.S. Application Data

(60) Provisional application No. 61/503,672, filed on Jul. 1, 2011.

(30) Foreign Application Priority Data

Aug. 18, 2011 (DE) .......................... 10 2011 081 167

(51) Int. Cl.
*G06K 9/00* (2006.01)
*A61B 6/00* (2006.01)

(52) U.S. Cl.
USPC ................ 382/132; 382/131; 378/4; 378/901

(58) Field of Classification Search
None
See application file for complete search history.

(56) References Cited

PUBLICATIONS

Ruye Wang, Introduction to Orthogonal Transforms, Pub Mar. 2006, pp. 261-268.*
Hiriyannaiah, Reconstruction from incomplete data in cone-beam tomography, Opt. Eng. 35(9), 1996, pp. 2748-2760.*
G.L. Zeng.: "Nonuniform Noise Propagation by Using the Ramp Filter in Fan-Beam Computed Tomography", IEEE Trans.Med.Imag. vol. 23 No. 6 pp. 690-695 (2004).
Dennerlein, et al.: "Fan-Beam Filtered-Backprojection Reconstruction without Backprotection Weight", Phys.Med. Biol. vol. 52 No. 11, pp. 3227-3239 (2007).
Dennerlein et al.: "Filtered Backprojection Reconstruction with depth-dependent Filtering", Tsinghua Science + Technology, vol. 15 No. 1, pp. 17-24 (2010).
Defrise et al. A Cone-Beam Reconstruction Algorithm Using Shift-Variant Filtering and Cone-Beam Backprojection IEEE, Transaction on Medical Imaging, vol. 13, No. 1 (1994).
Dennerlein et al., Avoiding the backprojection weight in short-scan CT reconstruction IEEE Nuclear Science Symposium Conference Record, pp. 2507-2509 (2009).
Dennerlein F., Fast Computation of the Redundancy Weighting Function Siemens AG, Healthcare Sector, Forchheim, Germany, Oct. 29, 2010, pp. 1-4.
Narasimhadhan et al., "Helical FDK Algorithms With No Backprojection Weight", Tencon 2009, pp. 1-5;( 2009).

* cited by examiner

*Primary Examiner* — David Zarka
*Assistant Examiner* — Ha Le
(74) *Attorney, Agent, or Firm* — Schiff Hardin LLP

(57) ABSTRACT

For filtered back-projection of a projection image data set, the projection image data set is cosine-weighted. The cosine-weighted projection image data set within the image plane of the projection image data set is subjected to a two-dimensional Radon transformation. The Radon transform of the cosine-weighted projection image data set differentiated with respect to the distance from an image origin of an image coordinate system. The derivative of the Radon transform is redundancy-weighted. The redundancy-weighted derivative is subjected to a two-dimensional Radon back-transformation. The Radon back-transform is differentiated and back-projected with respect to an image column coordinate. A differentiation step width entering into the differentiation is varied depending on depth.

6 Claims, 3 Drawing Sheets

BACK-PROJECTION OF A PROJECTION IMAGE DATA SET WITH DEPTH-DEPENDENT FILTERING

RELATED APPLICATION

The present application claims the benefit of the filing date of provisional application No. 61/503,672, filed on Jul. 1, 2011.

BACKGROUND OF THE INVENTION

1. Field of the Invention

The invention concerns a method for filtered back-projection of a projection image data set. The invention furthermore concerns a device and a non-transitory, computer-readable storage medium to implement the method.

2. Description of the Prior Art

In typical medical and non-medical methods (for example computed tomography) a projection image data set is used as an intermediate product in order to reconstruct, via back-projection, the three-dimensional, internal structure of an imaged subject. In the medical application, the subject is normally a body part of a patient.

The projection image data set is a series of projection images of the subject that were acquired at different projection angles in an image plane situated opposite the projection origin.

Computed tomography and similar imaging methods (for example rotation angiography) are x-ray acquisition methods. In these methods, an x-ray radiator is arranged in the projection origin, and the x-ray radiator radiates an x-ray beam through the subject to be examined onto an x-ray detector arranged in the image plane. In modern variants of computed tomography or rotation angiography, a conical x-ray beam (cone beam) is normally emitted by the x-ray radiator. The radiation transmitted through the subject is detected in two dimensions with spatial resolution at the detector.

The Feldkamp algorithm or the Clack-Defrise algorithm are conventionally used for the reconstruction of a projection image data set acquired in cone beam geometry. Both algorithms follow a common scheme; the projection image data set is consequently initially filtered and is subsequently projected back.

The Feldkamp algorithm is relatively uncomplicated mathematically and thus can be implemented quickly with simple means. However, it disadvantageously leads to significant image artifacts (shadows, for example) in the reconstructed 3D image data (tomogram) of the examined subject, in particular given acquisitions along only a portion of a circle, with a scan angle of less than 360°.

The Clack-Defrise algorithm is mathematically significantly more complicated than the Feldkamp algorithm; but it enables a significantly higher precision of the resulting 3D image data as a result of two-dimensional filter operations and due to a theoretically exact treatment of data redundancies.

However, it is common to both algorithms to take a weighting factor into account in the back-projection step, this weighting factor being inversely proportional to the quadratic interval (measured in the direction of a central beam of the cone beam geometry) of the projection origin relative to the spatial point (back-projection location) to be reconstructed. This weighting factor is also designated as a "back-projection weight".

The back-projection weight disadvantageously has a negative influence on the image quality because that it leads to an anisotropic spatial resolution in the resulting tomogram, as well as to a non-uniform distribution of the image noise; see F. Dennerlein, et al.: "Fan-beam filtered-backprojection reconstruction without backprotection weight", Phys. Med. Biol. 52(11):3227-3239, 2007; G. L. Zeng.: "Nonuniform noise propagation by using the ramp filter in fan-beam computed tomography", IEEE Trans. Med. Imag. 23(6):690-695, 2004).

From Dennerlein et al.: "Filtered backprojection reconstruction with depth-dependent filtering", Tsinghua Science+ Technology, 15(1):17-24, 2010, a method is known by means of which the back-projection weight is eliminated, and thus the image noise and the spatial resolution can be homogenized. This method is applicable without further measures to the Feldkamp algorithm but not to the Clack-Defrise algorithm. Given application to the later, the back-projection weight—and the disadvantages connected therewith—must therefore continue to be accepted.

An object of the invention is to enable a back-projection of a projection image data set acquired in a cone beam geometry, wherein the back-projection is particularly precise, low in artifacts, and homogeneous.

SUMMARY OF THE INVENTION

The method according to the invention proceeds from the conventional Clack-Defrise algorithm. As in this known algorithm, in the method according to the invention the projection image data set (more specifically its spatially dependent image value or greyscale value) is initially weighted (cosine-weighted) in a first method step with a weak cosine weighting function. In a second method step, the cosine-weighted projection image data set (resulting from the first method step) is subjected to a two-dimensional Radon transformation within the image plane of the projection image data set. The Radon transform that results from this is differentiated in a third method step with respect to a distance coordinate that reflects the distance of an image point from an origin of an image coordinate system.

In a fourth method step, the (first) derivate resulting from the third method step is—similar to the classical Clack-Defrise algorithm—weighted (redundancy-weighted) by means of a weak redundancy weighting function. This compensates the effect that, due to the cone beam projection geometry, in the case of partial circular acquisitions, the spatial regions of the subject that are located near the center of the scan trajectory are imaged with higher redundancy than the regions of the subject near the gaps of the scanning path.

In a departure from the conventional Clack-Defrise algorithm in which the result of the redundancy weighting—i.e. the redundancy-weighted (first) derivative—is differentiated again with respect to the distance coordinate, and is only Radon-transformed back again afterwards, in the method according to the invention the redundancy-weighted (first) derivative is subjected to a two-dimensional Radon back-transformation in a fifth method step, without prior second differentiation.

The Radon back-transform resulting from this is then differentiated in a sixth method step during the back-projection according to a column coordinate of the image coordinate system. The differentiation in this step is varied depending on depth, i.e. depending on the back-projection location.

The method according to the invention thus differs from the conventional Clack-Defrise algorithm due to the reverse order of the second differentiation process and the Radon back-transformation. It is thus achieved that the filter operations of the method according to the invention end in the second differentiation. This in turn enables the second differentiation to be mathematically contracted with the back-projection.

The differentiation step width that is required for the second differentiation can be used, as is known, as an additional degree of freedom in order to optimize the image quality via depth-dependent modification of this differentiation step width. In particular, the back-projection weight can be decreased or even completely eliminated in the known manner by an appropriate variation of the differentiation step width, so a homogenization of the spatial resolution and of the image noise is achieved.

In a preferred embodiment, the device according to the invention has a reconstruction module that is configured in terms of circuitry and/or programming to automatically implement the method according to the invention in any embodiment. The reconstruction module can be a software module in which the instructions required to automatically implement the method are realized in terms of software, and that is implemented so as to be capable of running in a computer.

In a preferred embodiment, the device is also additionally equipped with means to acquire the projection image data set. In particular, the device is a computed tomography apparatus or an x-ray C-arm system that has an x-ray imaging arrangement (composed of an x-ray radiator and an x-ray detector) to acquire the projection image data set, as well as a control and evaluation computer with the reconstruction module implemented therein. In another embodiment, the device can be an isolated evaluation computer to which the projection image data set is supplied from an external image acquisition unit or from an image memory.

The present invention also encompasses a non-transitory, computer-readable data storage medium encoded with programming instructions (control commands) that, when the storage medium is loaded into a computerized control system of a tomographic imaging system, cause the computerized control system to operate the tomographic imaging system to execute one or more of the embodiments of the above-described invented method. The programming instructions can be executed as programming code in a commercially available mathematics program, such as Matlab®.

DESCRIPTION OF THE PREFERRED EMBODIMENTS

Figure 1:
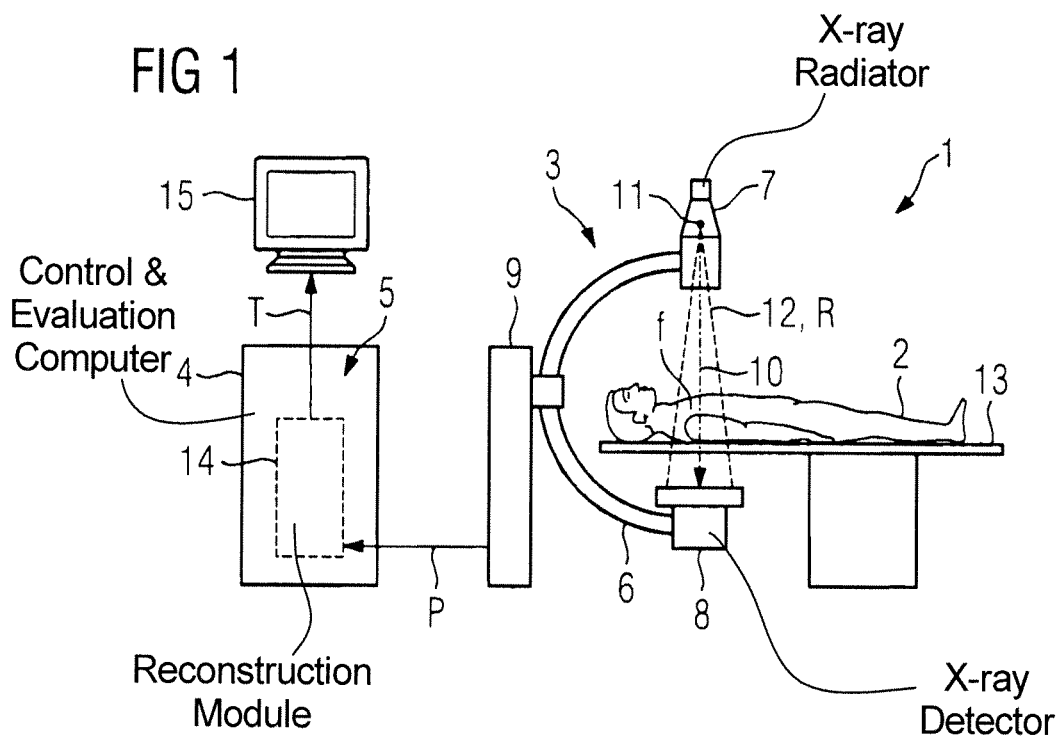
FIG. 1 schematically illustrates an x-ray C-arm system, with a C-arm on which an x-ray radiator and a flat panel x-ray detector are arranged opposite to one another, as well as with a control and evaluation computer in which a reconstruction module for filtered back-projection of a projection image data set.

Parts, variables and structures corresponding to one another are always provided with the same reference characters in all figures.

The device 1 shown in FIG. 1 serves to acquire a projection image data set P of a region of the inside of the body of a patient 2. The device 1 furthermore serves to reconstruct a three-dimensional image data set (subsequently designated as a tomogram T) from the projection image data set P that reflects the examined region of the inside of the body.

The C-arm apparatus 3 includes a C-arm 6 with an x-ray radiator 7 and an x-ray detector 8 mounted opposite to one another. The C-arm 6 is supported on a base 9. The C-arm 6 can be rotated relative to this base 9 around a horizontal axis. It can additionally be panned along the arc line (i.e. in the plane spanned by the C-arm 6).

A central beam 10 of the C-arm apparatus 3 thus can be set in virtually arbitrary orientations relative to the surrounding space. That spatial vector that links a focus 11 of the x-ray radiator 7 with a center of the x-ray detector 8 and that hereby in particular is aligned perpendicular to the detector surface is hereby designated as a central beam 10. The central beam 10 forms the center of a conical x-ray beam (subsequently designated as a cone beam 12) that, during operation of the C-arm apparatus 3, is radiated—starting from the focus 11—onto the two-dimensional detector surface of the x-ray detector 8.

Associated with the C-arm apparatus 3 is a patient table 13 on which the patient can be supported such that the body region of the patient 2 that is to be examined is arranged in the acquisition region of the C-arm 3.

The inventive procedure implemented in the computer 4 is executed by a reconstruction module 14 (hardware or software).

Figure 2:
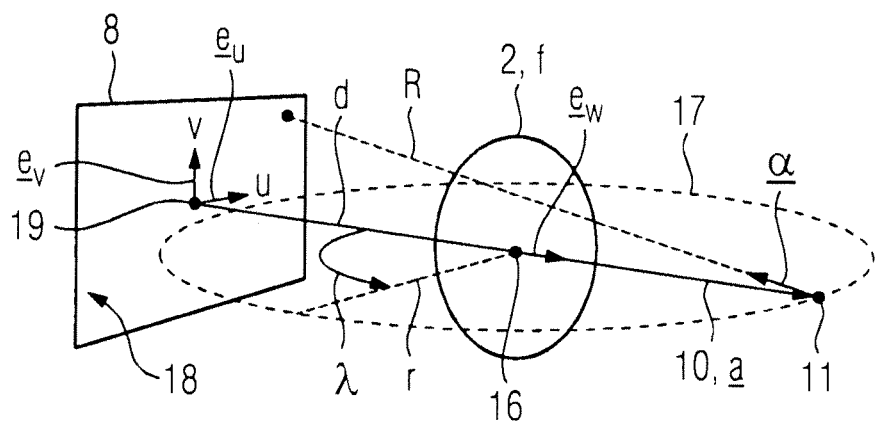
FIG. 2 is a schematic, simplified representation of the x-ray radiator, the x-ray detector and a subject placed between them.

To acquire the projection image data set P, the x-ray radiator 7 and the x-ray detector 8 are driven around the patient 2 on a path (orbit) corresponding to a partial or complete circle, wherein the patient 2 is exposed with x-ray radiation R from various projection angles λ (FIG. 2). The projection image data set P accordingly is a series of two-dimensional projection images that depict the body region of the patient 2 that is to be examined from the different projection angles λ.

The projection image data set P is supplied to the computer 4 via the C-arm 3. The reconstruction module 14 implemented in the computer 4 calculates the tomogram T from the projection image data set P in the manner described in detail in the following, which tomogram T can subsequently be displayed in the form of slice representations, rendered 3-D views, or in another known presentation form via a monitor 15.

Structures inside the body are depicted in the projection image data set capital due to the physical fact that the human body has both a tissue type-dependent (and thus also a spatially dependent) x-ray attenuation coefficient f that can consequently be written as a mathematical function of the location x within (and possibly outside of) the patient body:

$$f = f(\underline{x}).  \qquad \text{EQ 1}$$

The location x is hereby specified in units of a three-dimensional spatial coordinate system whose origin 16—according to FIG. 2—is, by convention, placed approximately centrally in the body region of the patient 2 that is to be examined, for example.

The position of the focus 11 that forms the projection center for the projection image data set P is described by a spatial vector a. The unit vector parallel to the spatial vector a is designated with $\underline{e}_w$. Given the rotation of the focus 11 on a circular rotation orbit 17 around the origin 16, the spatial vector a has a constant length that is subsequently designated as a radius r, as well as an orientation dependent on the projection angle λ. In the spatial coordinate system (that is appropriately defined as a cylinder coordinate system), the spatial vector a can thus be written as $$\underline{a}(\lambda) = r \cdot \underline{e}_w(\lambda) = (r \cos \lambda, r \sin \lambda, 0). \qquad \text{EQ 2}$$

Given a rotation of the focus 11 around a partial circle, the projection angle λ thereby varies between the limit values $\lambda_{min}$ and $\lambda_{max}$ ($\lambda \in [\lambda_{min}, \lambda_{max}]$).

Figure 3:
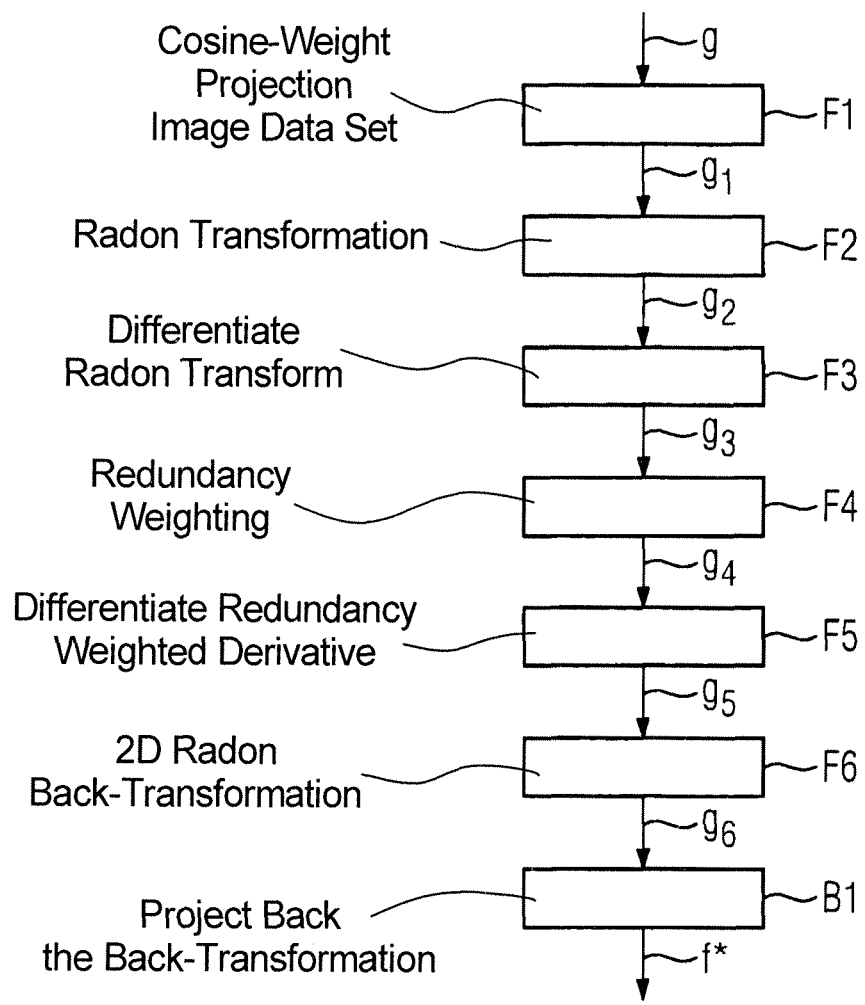
FIG. 3 is a flowchart of the Clack-Defrise algorithm for filtered back-projection of projection data in its known form.

The surface of the x-ray detector 8 is always located at a constant distance d from the focus 11. This detector surface forms an image plane 18 for each of the projection images of the projection image data set P. Each image point of the projection image data set P is characterized by an image value g (FIG. 3), i.e. a color value or a greyscale value. This image value g is hereby dependent on a (column) coordinate u and a (line) coordinate v. The coordinates u and v form a Cartesian image coordinate system with an origin lying in the image plane 18 and associated unit vectors $\underline{e}_u$ or, respectively, $\underline{e}_v$ that, in the spatial coordinate system, have the coordinates (depending on the projection angle λ)

$$\underline{e}_u = \underline{e}_u(\lambda) = (-\sin \lambda, \cos \lambda, 0) \qquad \text{EQ 3}$$

$$\underline{e}_v = \underline{e}_v(\lambda) = (0, 0, 1) \qquad \text{EQ 4}$$

The image value g is also dependent on the projection angle λ and can thus be functionally written as $$g = g(u, v, \lambda) \qquad \text{EQ 5}$$

The individual projection images of the projection image data set P hereby differ due to a different value of the projection angle λ that is, however, constant for each projection image.

In the sense of the notation introduced in the preceding, the image value g of the projection image data set P is functionally provided by $$g = g(\lambda, u, v) = \int_{-\infty}^{\infty} f(\underline{a}(\lambda) + t\underline{\alpha}(\lambda, u, v)) \cdot dt \qquad \text{EQ 6}$$

wherein α (with α=α(λ,u,v)) herein designates the unit vector along that x-ray beam that emanates from the focus 11 and intersects the image plane 18 in the image point with the coordinates u and v.

The problem to be solved in the course of the reconstruction is to find a function (designated in the following as a "reconstructed" attenuation f* (FIG. 3)) that optimally precisely maps the function of the spatially dependent x-ray attenuation coefficient f, wherein the tomogram T is derived from this "reconstructed" attenuation f* (with f*=f*(x)).

The reconstruction module 14 uses a modified Clack-Defrise algorithm for the reconstruction.

In the conventionally known form of the Clack-Defrise algorithm—for example from M. Defrise, R. Clack: "A cone-beam reconstruction algorithm using shift-invariant filtering and cone-beam backprojection", IEEE Trans. Med. Imag., 13(1): 186-195, 1994—the projection image data set P (more precisely the spatially dependent image value g of the projection image data set P) is initially weighted in a first method step F1 according to FIG. 3 with a weak cosine direction function:

$$g_1 = g_1(\lambda, u, v) = \frac{d}{\sqrt{d^2 + u^2 + v^2}} \cdot g(\lambda, u, v) \qquad \text{EQ 7}$$

In a subsequent second method step F2, the weighted projection image data set P (more precisely the image value $g_1$ resulting from EQ 7) is subjected to a two-dimensional Radon transformation:

$$g_2 = g_2(\lambda, \mu, s) = \int_{-\infty}^{\infty} g_1(\lambda, s \cdot \cos \mu - t \cdot \sin \mu, s \cdot \sin \mu + t \cdot \cos \mu) \cdot dt \qquad \text{EQ 8}$$

Figure 4:
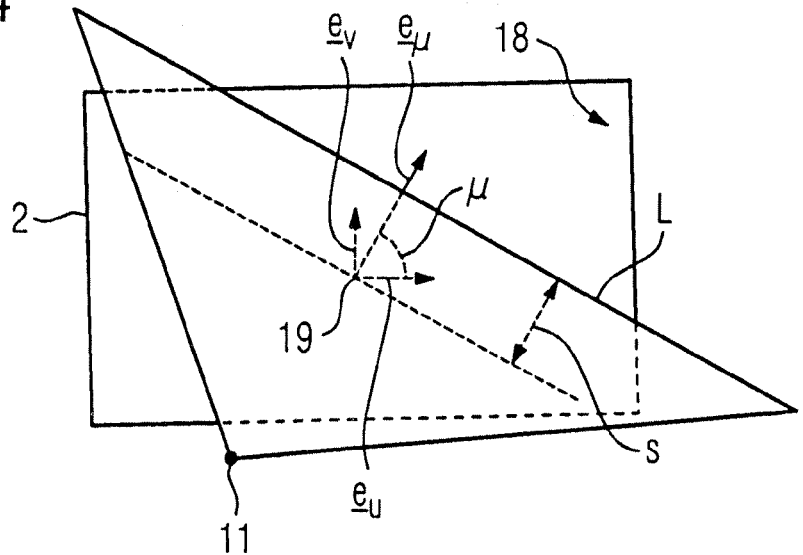
FIG. 4 schematically shows the detector surface of the x-ray projector as well as a projection plane intersecting the detector surface.

Line integrals over the weighted image value $g_1$ are hereby formed, as is indicated in FIG. 4. Each line L is hereby parameterized by an (inclination) coordinate μ with associated unit vector $\underline{e}_\mu$ and a distance coordinate s, wherein the coordinates μ and s arise as polar coordinates from the Cartesian image coordinate system:

$$u = s \cdot \cos \mu \qquad \text{EQ 9}$$

$$v = s \cdot \sin \mu \qquad \text{EQ 10}$$

In a third method step F3 of the known Clack-Defrise algorithm, the Radon transform $g_2$ resulting from EQ 8 is differentiated with respect to the distance coordinate s:

$$g_3 = g_3(\lambda, \mu, s) = \frac{\partial}{\partial s} g_2(\lambda, \mu, s) \qquad \text{EQ 11}$$

In a fourth method step F4, the derivative $g_3$ resulting from EQ 11 is weighted with a weak (redundancy) weighting function M that compensates for redundancies in the projection image data set P on a theoretically exact basis:

$$g_4 = g_4(\lambda, u, v) = \frac{1}{\sqrt{4\pi^2}} \frac{r}{d} \cdot M(\lambda, u, s) \cdot \cos \mu \cdot g_3(\lambda, u, s) \qquad \text{EQ 12}$$

The redundancy weighting function M (with M=M(λ,μ,s)) that enters into EQ 12 can thereby in particular be specified as follows:

$$M(\lambda, \mu, s) = \frac{|\cos \mu|^m}{2|\cos \mu|^m + 2\{1 - ((s/d)\cos \lambda - \cos \mu \cdot \sin \lambda)^2\}_+^{m/2}} \qquad \text{EQ 13}$$

The operator { . . . }, used in EQ 13 has the property $$\{x\}_+ = \begin{cases} x & \text{if } x > 0 \\ 0 & \text{otherwise} \end{cases} \qquad \text{EQ 14}$$

The parameter m has a value strongly exceeding the number 2.

In a fifth method step F5, the redundancy-weighted derivative $g_4$ resulting from EQ 13 in the known Clack-Defrise algorithm is differentiated with respect to the distance coordinate s:

$$g_5 = g_5(\lambda, \mu, s) = \frac{\partial}{\partial s} g_4(\lambda, \mu, s) \qquad \text{EQ 15}$$

In a sixth method step F6, the derivative $g_5$ resulting from EQ 15 is subjected to a two-dimensional Radon back-transformation:

$$g_6 = g_6(\lambda, u, v) = \int_{-\pi/2}^{\pi/2} g_5(\lambda, \mu, u \cdot \cos \mu + v \cdot \sin \mu) \cdot d\mu \qquad \text{EQ 16}$$

The back-transform $g_6$ resulting from EQ 16 is projected back in a final method step B1.

$$f*(x) = \int_{\lambda_{in}}^{\lambda_{out}} \frac{rd}{[r - \underline{x} \cdot \underline{e}_w(\lambda)]^2} g_6(\lambda, u^*, v^*) \cdot d\lambda \qquad \text{EQ 17}$$

A factor $[r-\underline{x} \cdot e_w(\lambda)]^{-2}$ that is dependent on the square of the distance of the location $\underline{x}$ from the image plane 18 hereby enters into the back-projection, which factor forms the aforementioned back-projection weight. The variables u* and v* in EQ 17 respectively designate those coordinates u and v of the image coordinate system at which the back-projection beam traversing the back-projection location $\underline{x}$ and the focus F intersects the image plane 18.

Figure 5:
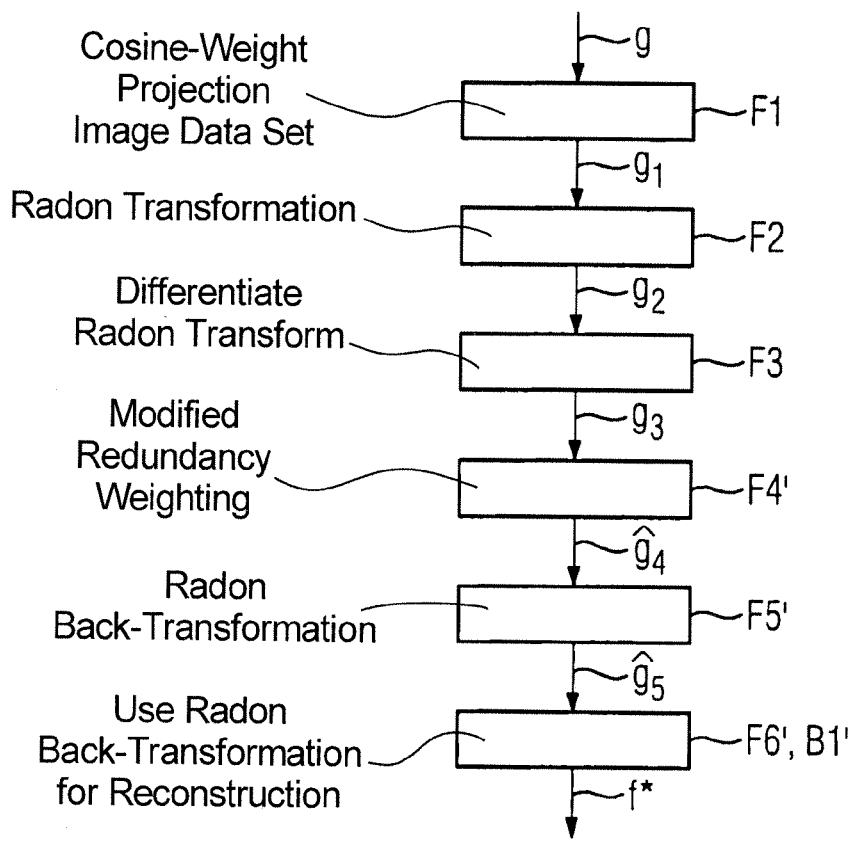
FIG. 5 is a flowchart of a further embodiment of the method according to the invention for filtered back-projection of the projection image data set.

In a variant implemented by the reconstruction module 14 and explained in FIG. 5, the method according to the invention implements the steps F1, F2 and F3 of the conventional Clack-Defrise algorithm.

As in the latter, a redundancy weighting is also made in the fourth method step F4' in the method according to the invention. However, for this the reconstruction module 14 uses an Equation that is modified relative to the classical Clack-Defrise algorithm $$\hat{g}_4 = \hat{g}_4(\lambda, \mu, s) = -\frac{1}{4\pi^2} \frac{r}{d} M(\lambda, \mu, s) \cdot g_3(\lambda, \mu, s) \qquad \text{EQ 18}$$

Instead of the second derivation step F5 of the Clack-Defrise algorithm, in a fifth method step F5' the reconstruction module 14 directly uses the Radon back-transformation on the redundancy-weighted derivation $\hat{g}_4$ that resulted from EQ 18:

$$\hat{g}_5 = \hat{g}_5(\lambda, u, v) = \int_{-\pi/2}^{\pi/2} \hat{g}_4(\lambda, \mu, u \cdot \cos \mu + v \cdot \sin \mu) \cdot d\mu \qquad \text{EQ 19}$$

In a following method step F6', the Radon back-transform $\hat{g}_5$ is differentiated by the reconstruction module 14 according to the image column coordinate u.

However, according to the invention this derivation is not made as an isolated calculation operation. Rather, the derivation is made together with a final back-projection step B1':

$$f^* = \qquad \text{EQ 20}$$
$$f^*(\underline{x}) = \frac{rd}{2\varepsilon} \int_{\lambda_{in}}^{\lambda_{out}} [\hat{g}_5(\lambda, u^* + \Delta u^*, v^*) - \hat{g}_5(\lambda, u^* - \Delta u^*, v^*)] \cdot d\lambda$$

In EQ 20, δu* designates a derivation step width that is varied depending on the back-projection location x.

In order to arrive at Equation 20, the derivation step width δu* is established according to $$\Delta u^* = \Delta u^*(\lambda, \underline{x}) = \epsilon \cdot [r - \underline{x} \cdot e_w(\lambda)]^{-2} \qquad \text{EQ 21}$$

wherein ε designates a constant that is chosen to be sufficiently small so that the derivation step width δu* is less than the width of an image point within the image plane 18 (i.e. smaller than the width of a detector pixel). The back-projection weight from the back-projection formula is precisely eliminated via this selection of the derivation step width δu*. Within the scope of the invention, however, the derivation step width δu* can also be selected differently. In particular, the derivation step width δu* can be selected particularly small in spatial regions in which a particularly high image quality is required, and larger in other spatial regions in which the image quality is less significant.

In a special embodiment of the invention, the reconstruction module 14 is designed as a separate computer program product with which a conventional C-arm system can be equipped or that is capable of running in isolation on a computer to reconstruct a stored projection image data set P. In the latter variant, the reconstruction module 14 can in particular be implemented as a MATLAB® program.

Although modifications and changes may be suggested by those skilled in the art, it is the intention of the inventors to embody within the patent warranted hereon all changes and modifications as reasonably and properly come within the scope of their contributions to the art.

We claim as our invention:

1. A method for filtered back-projection of a projection image data set, consisting of:

providing a projection image data set, acquired by panning an x-ray source through a plurality of projection angles with respect to an image plane, to a processor and, in said processor, cosine-weighting said projection image data set to obtain a cosine-weighted projection image data set $g_1$;

in said processor, subjecting the cosine-weighted projection image data set $g_1$ within said image plane to a two-dimensional Radon transformation according to a Radon transform $g_2$;

in said processor, differentiating the Radon transform $g_2$ of the cosine-weighted projection image data set $g_1$ with respect to a distance from an image origin of an image coordinate system, to obtain a differentiated Radon transform $g_3$;

in said processor, redundancy-weighting the differentiated Radon transform $g_3$, to obtain a redundancy-weighted derivative $\hat{g}_4$, in said processor, subjecting the redundancy-weighted derivative $\hat{g}_4$ to a two-dimensional Radon back-transformation, thereby obtaining a Radon back-transform $\hat{g}_5$; and in said processor, differentiating and back-projecting the Radon back-transform $\hat{g}_5$ with respect to an image column coordinate u with differentiation step with delta u*, and varying said differentiation step with delta u* depending on depth.

2. A method as claimed in claim 1, comprising:

redundancy-averaging the derivative ($g_3$) of the Radon transform ($g_2$) according to $$\hat{g}_4 = \hat{g}_4(\lambda, \mu, s) = -\frac{1}{4\pi^2} \frac{r}{d} M(\lambda, \mu, s) \cdot g_3(\lambda, \mu, s)$$

wherein λ is the projection angle, μ is the polar angle without inclination coordinate within the image plane, s is the distance from the origin of the image coordinate system, r is the distance of a projection center to the center point of a rotation circle along which the projection center is panned during variation of the projection angle λ, d is the distance of the projection center from the image plane, M is a redundancy weighting function, $g_3$ is the derivative of the Radon transform ($g_2$), and $\hat{g}_4$ is the resulting redundancy-weighted derivative.

3. A method according to claim 1, comprising:

implementing the back-projection of the Radon back-transform ($\hat{g}_5$) and the derivative with respect to the image line coordinate (u) according to $$f^* = f^*(\underline{x}) = \frac{rd}{2\varepsilon} \int_{\lambda_{out}}^{\lambda_{in}} [\hat{g}_5(\lambda, u^* + \Delta u^*, v^*) - \hat{g}_5(\lambda, u^* - \Delta u^*, v^*)] \cdot d\lambda$$

wherein x is the location of a spatial volume (back-projection location) to be reconstructed, f* is the reconstructed attenuation, r is the distance of a projection center from the center point of a rotation circle along which the projection center is panned during variation of the projection angle, d is the distance of the projection center from the image plane, λ is the projection angle, $\lambda_{in}$ and $\lambda_{out}$ are the limits of a projection angle range, u* and v* are the image column coordinates or, respectively, image line coordinates of the image point in which the back-projection beam traversing the projection origin and the back-projection location (x) intersects the image plane, Δu* is the derivation step width, $\hat{g}_5$ is the Radon back-transform, and ε is a constant number.

4. A method according to claim 3, comprising:
setting the derivation step width (Δu*) according to $$\Delta u^* = \varepsilon \cdot [R - \underline{x} \cdot \underline{e}_w(\lambda)]^{-2}$$

wherein $e_w$ is the unit vector of the line connecting the center point of the rotation circle with the projection center.

5. An apparatus for filtered back-projection of a projection image data set consisting of:
a processor having an input that receives a projection image data set, acquired by panning an x-ray source through a plurality of projection angles with respect to an image plane, to a processor, and a reconstruction module configured to cosine-weight said projection image data set to obtain a cosine-weighted projection image data set $g_1$;
processor reconstruction module being configured to subject the cosine-weighted projection image data set $g_1$ within said image plane to a two-dimensional Radon transformation according to a Radon transform $g_2$;
said reconstruction module being configured to differentiate the Radon transform $g_2$ of the cosine-weighted projection image data set $g_1$ with respect to a distance from an image origin of an image coordinate system, to obtain a differentiated Radon transform $g_3$;
said reconstruction module being configured to redundancy-weight the differentiated Radon transform $g_3$, to obtain a redundancy-weighted derivative $\hat{g}_4$;
said reconstruction module being configured to subject the redundancy-weighted derivative $\hat{g}_4$ to a two-dimensional Radon back-transformation, thereby obtaining a Radon back-transform $\hat{g}_5$; and
said reconstruction module being configured to differentiate and back-project the Radon back-transform $\hat{g}_5$ with respect to an image column coordinate u with differentiation step with delta u*, and varying said differentiation step with delta u* depending on depth.

6. A non-transitory, computer-readable data storage medium encoded with programming instructions, said data storage medium being loaded into a computerized control system of a tomographic imaging system and said programming instructions causing said computerized control system to execute a procedure consisting of:
receive a projection image data set, acquired by panning an x-ray source through a plurality of projection angles with respect to an image plane, to a processor and cosine-weight said projection image data set to obtain a cosine-weighted projection image data set $g_1$;
subject the cosine-weighted projection image data set $g_1$ within said image plane to a two-dimensional Radon transformation according to a Radon transform $g_2$;
differentiate the Radon transform $g_2$ of the cosine-weighted projection image data set $g_1$ with respect to a distance from an image origin of an image coordinate system, to obtain a differentiated Radon transform $g_3$;
redundancy-weight the differentiated Radon transform $g_3$, to obtain a redundancy-weighted derivative $\hat{g}_4$;
subject the redundancy-weighted derivative $\hat{g}_4$ to a two-dimensional Radon back-transformation, thereby obtaining a Radon back-transform $\hat{g}_5$; and
differentiate and back-project the Radon back-transform $\hat{g}_5$ with respect to an image column coordinate u with differentiation step with delta u*, and varying said differentiation step with delta u* depending on depth.

* * * * *